US011337701B2

(12) United States Patent
Williams et al.

(10) Patent No.: US 11,337,701 B2
(45) Date of Patent: May 24, 2022

(54) DEVICES AND METHODS FOR ASSEMBLING ADAPTER ASSEMBLIES

(71) Applicant: Covidien LP, Mansfield, MA (US)

(72) Inventors: Justin Williams, Southbury, CT (US); Ramiro Cabrera, Cheshire, CT (US); Joseph Eisinger, Northford, CT (US); Anthony Sgroi, Jr., Wallingford, CT (US); David Valentine, Jr., Hamden, CT (US)

(73) Assignee: Covidien LP, Mansfield, MA (US)

( * ) Notice: Subject to any disclaimer, the term of this patent is extended or adjusted under 35 U.S.C. 154(b) by 93 days.

(21) Appl. No.: 16/788,383

(22) Filed: Feb. 12, 2020

(65) Prior Publication Data

US 2020/0275932 A1 Sep. 3, 2020

Related U.S. Application Data

(60) Provisional application No. 62/812,554, filed on Mar. 1, 2019.

(51) Int. Cl.
*A61B 17/115* (2006.01)
*A61B 17/34* (2006.01)
*A61B 17/00* (2006.01)

(52) U.S. Cl.
CPC ...... *A61B 17/1155* (2013.01); *A61B 17/3417* (2013.01); *A61B 2017/00486* (2013.01)

(58) Field of Classification Search
CPC .......................... A61B 17/1155; A61B 17/3417
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Oct. 7, 2020, corresponding to counterpart European Application No. 20160181.2; 14 pages.

(Continued)

*Primary Examiner* — Nathaniel C Chukwurah
(74) *Attorney, Agent, or Firm* — Carter, DeLuca & Farrell LLP

(57) ABSTRACT

A device for loading a trocar assembly with an adapter assembly of a surgical stapling instrument is provided. The trocar loading device includes a base member and an engagement member operatively secured to the base member. The base member defines a longitudinal passage for receipt of a trocar assembly and the engagement member releasably secures the trocar member within the base member. The base member includes an alignment feature for aligning the trocar assembly with an adapter assembly.

20 Claims, 14 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,023,014 B2 | 5/2015 | Chowaniec et al. |
| 9,055,943 B2 | 6/2015 | Zemlok et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |

(56) References Cited

U.S. PATENT DOCUMENTS

| | | |
|---|---|---|
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0106406 A1 | 4/2016 | Cabrera et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0086879 A1 | 3/2017 | Williams |
| 2017/0340348 A1* | 11/2017 | Cabrera ............. A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1815805 A1 | 8/2007 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3103402 A1 | 12/2016 |
| EP | 3123959 A1 | 2/2017 |
| EP | 3593736 A2 | 1/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 03066122 A2 | 8/2003 |
| WO | 2008107918 A1 | 9/2008 |
| WO | 2010059574 A2 | 5/2010 |

OTHER PUBLICATIONS

European Search Report dated Jul. 3, 2020, issued in EP Appln. No. 20160181, 17 pages.

* cited by examiner

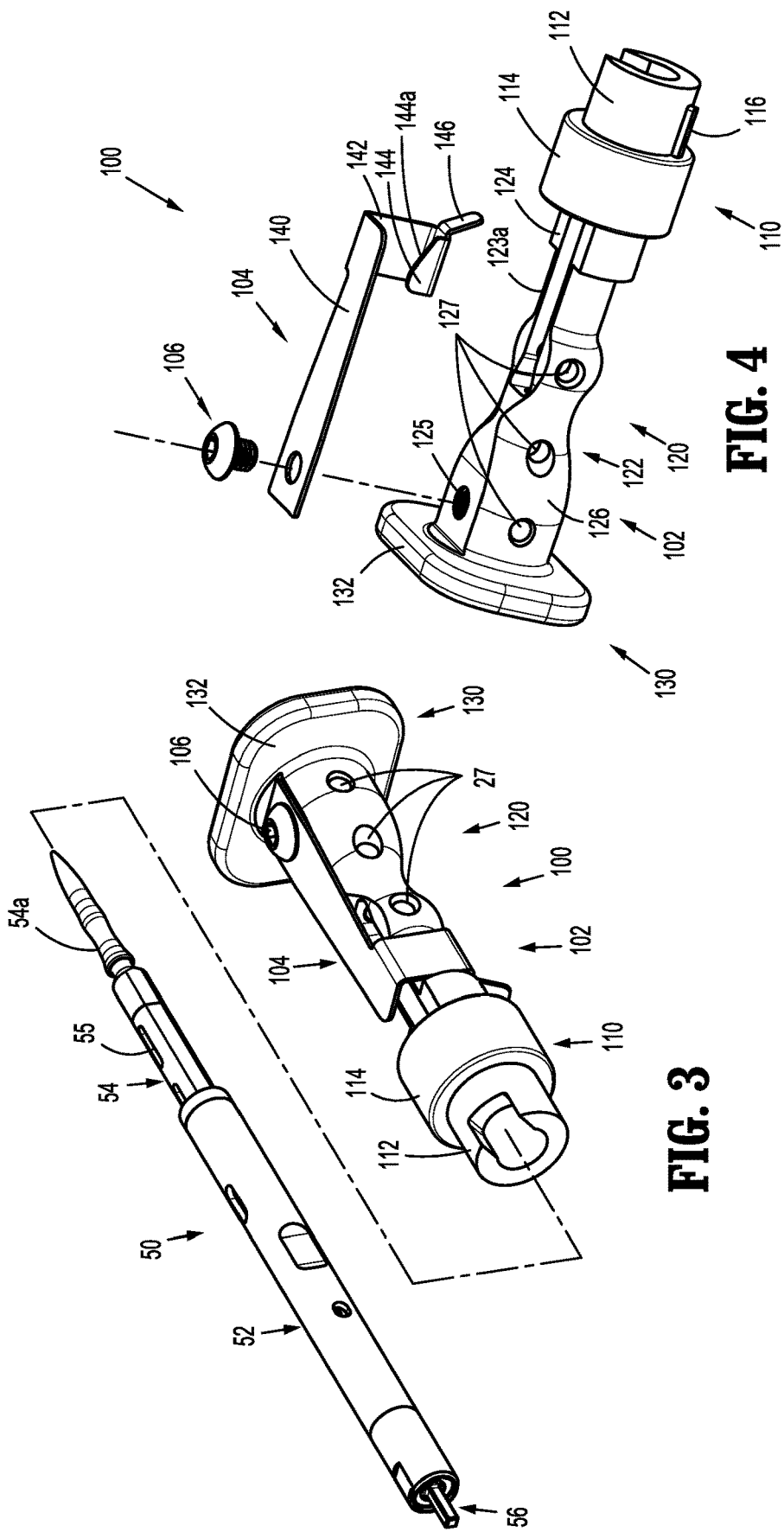

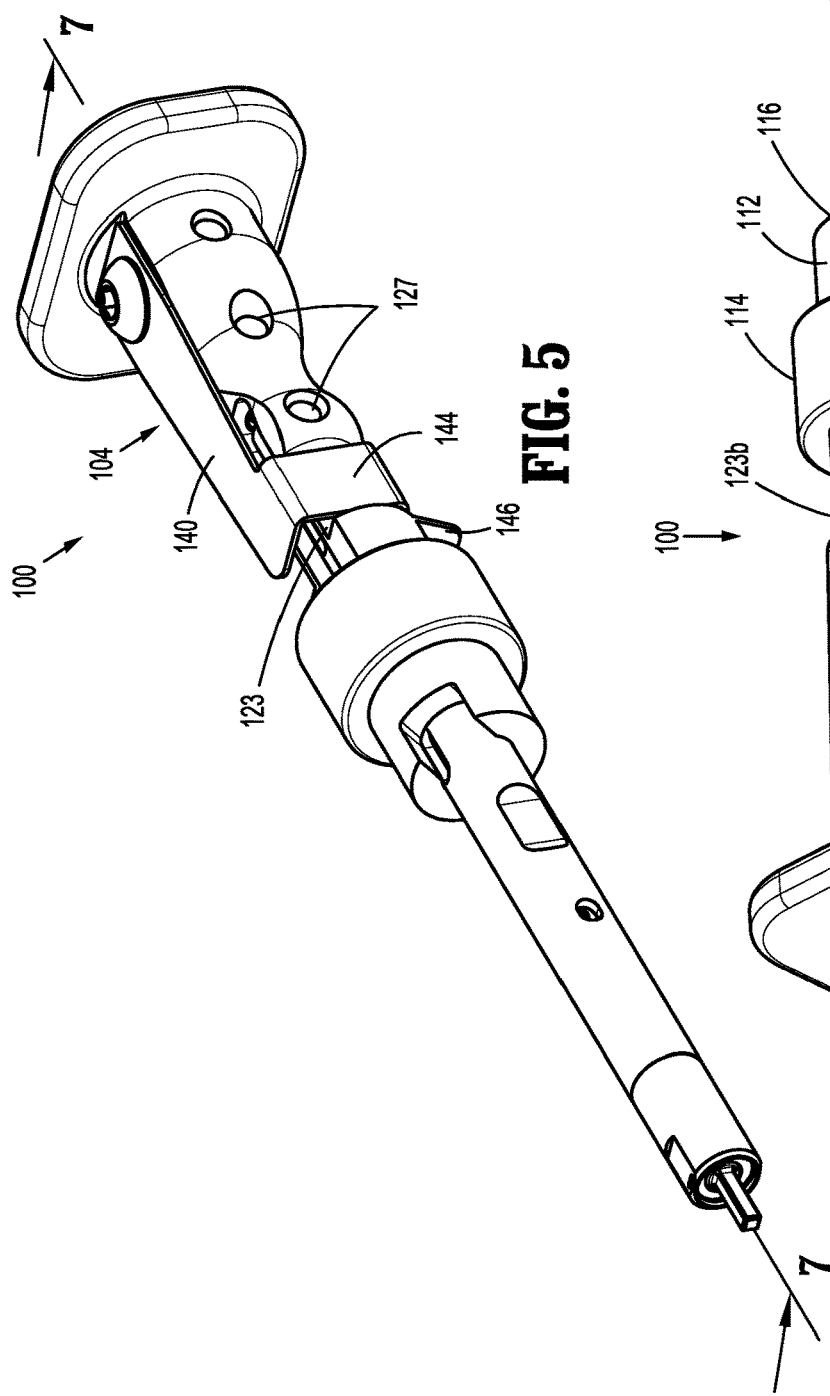
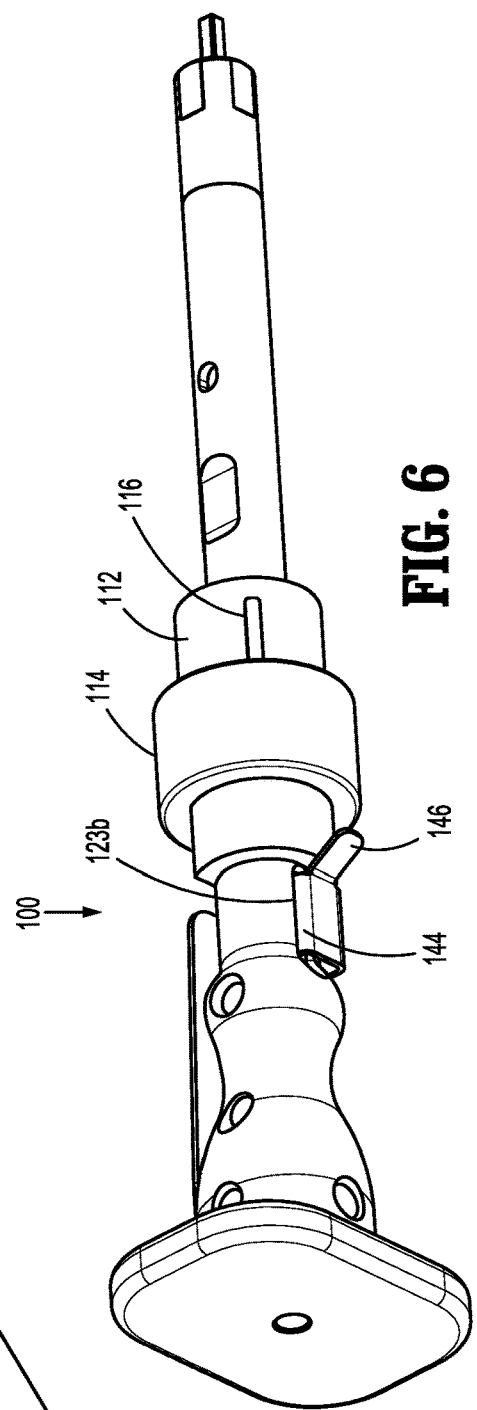

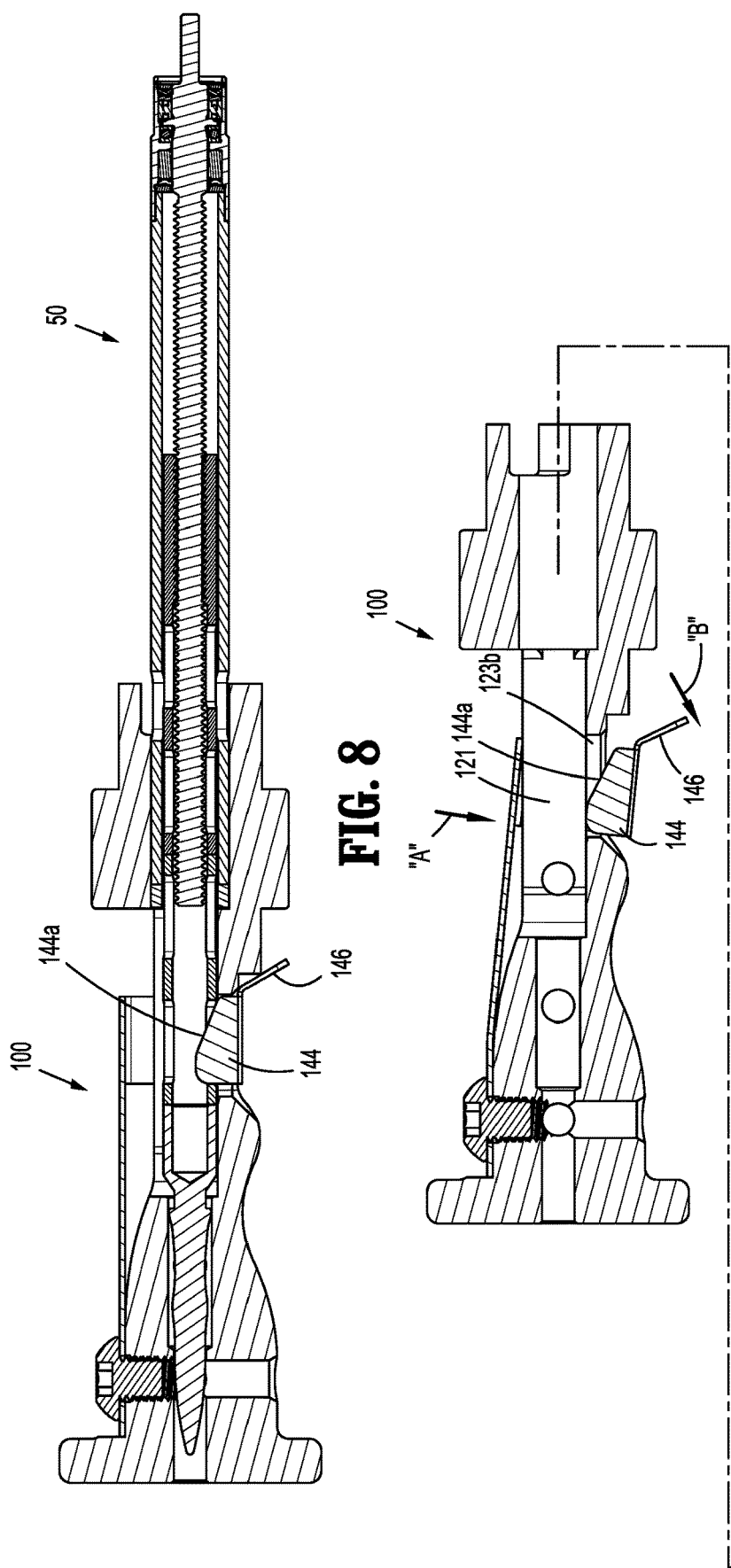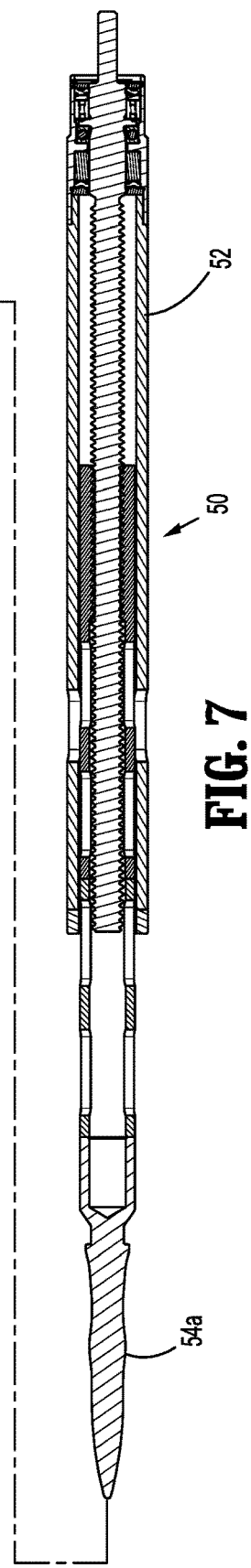

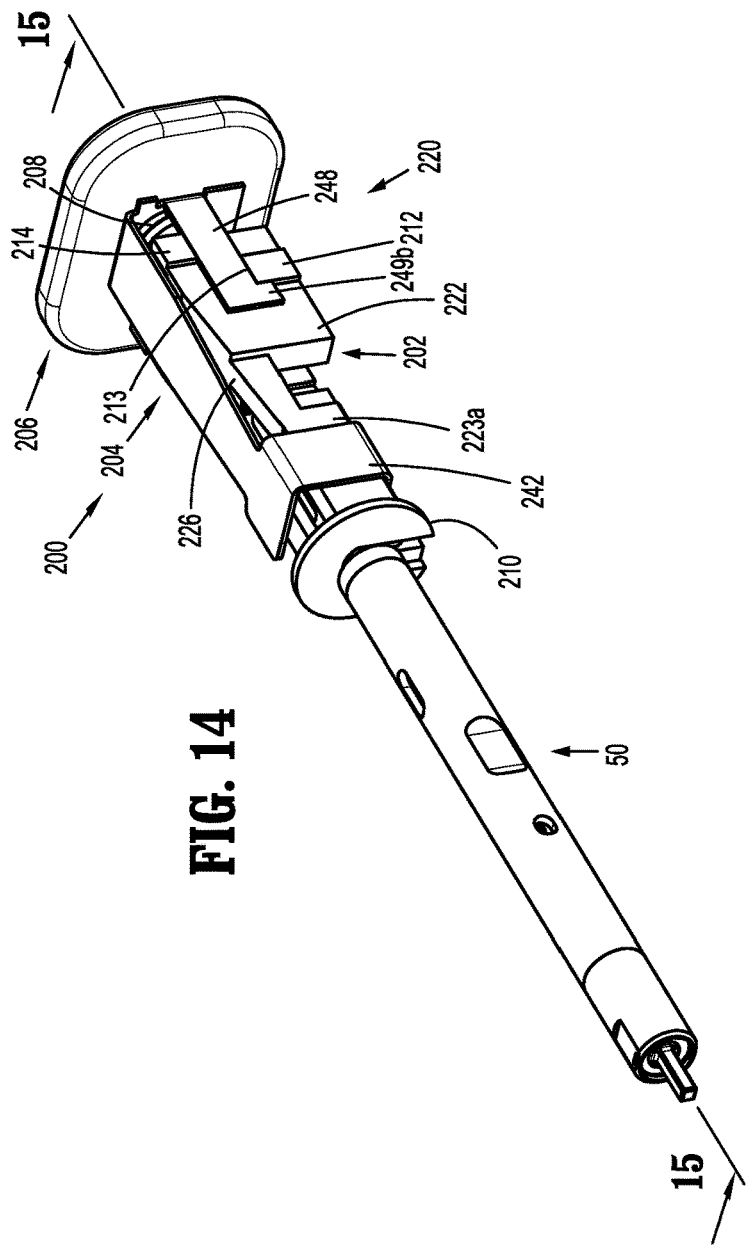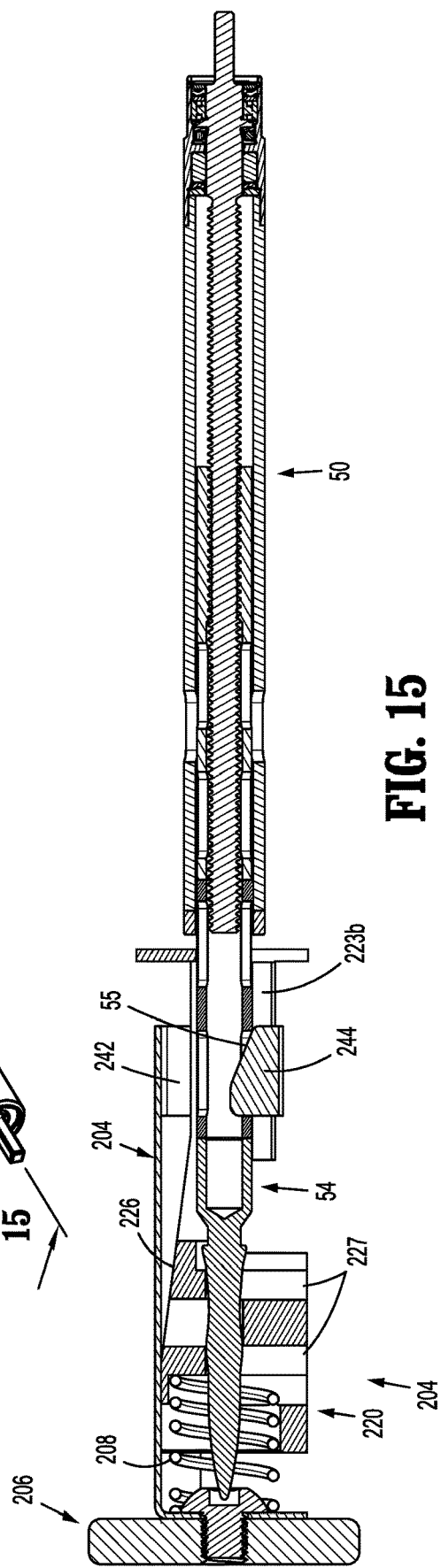

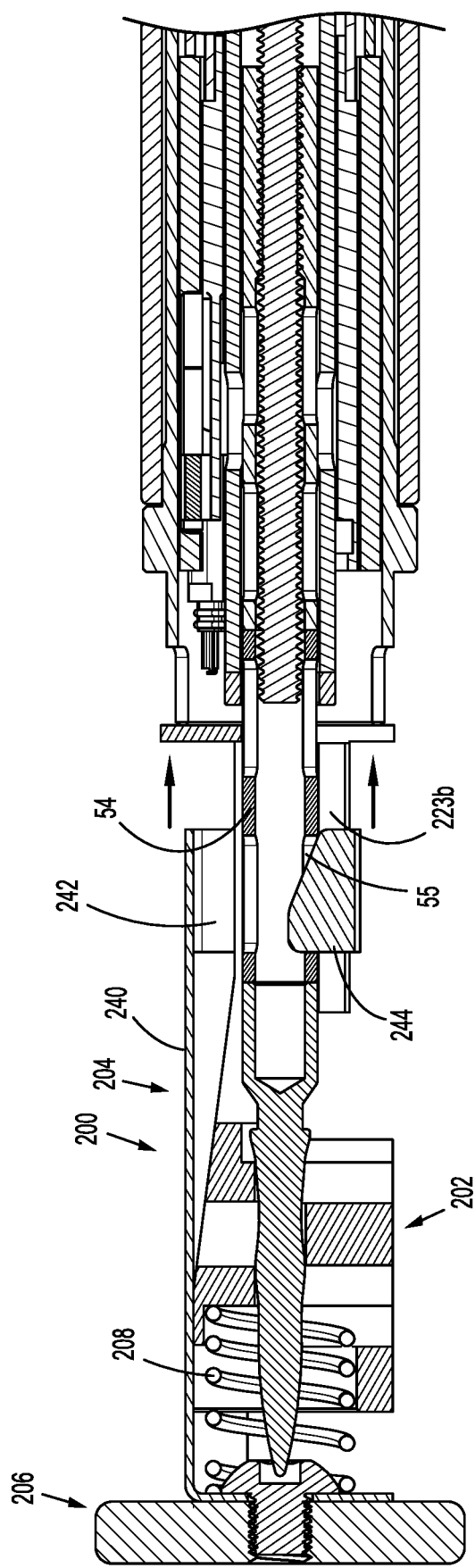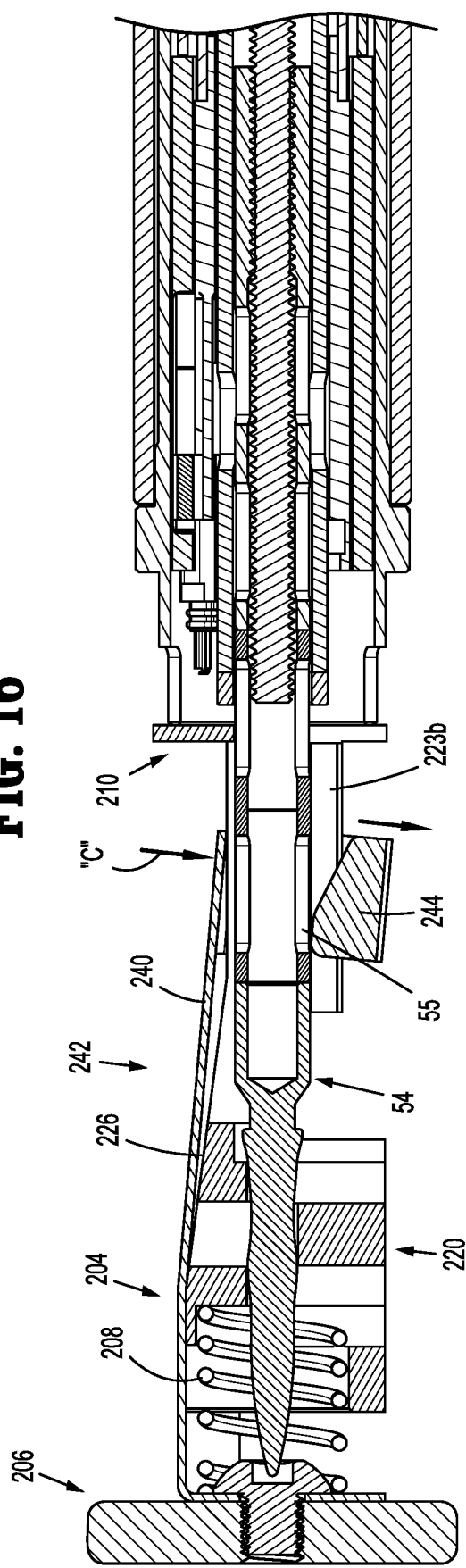
FIG. 16
FIG. 17

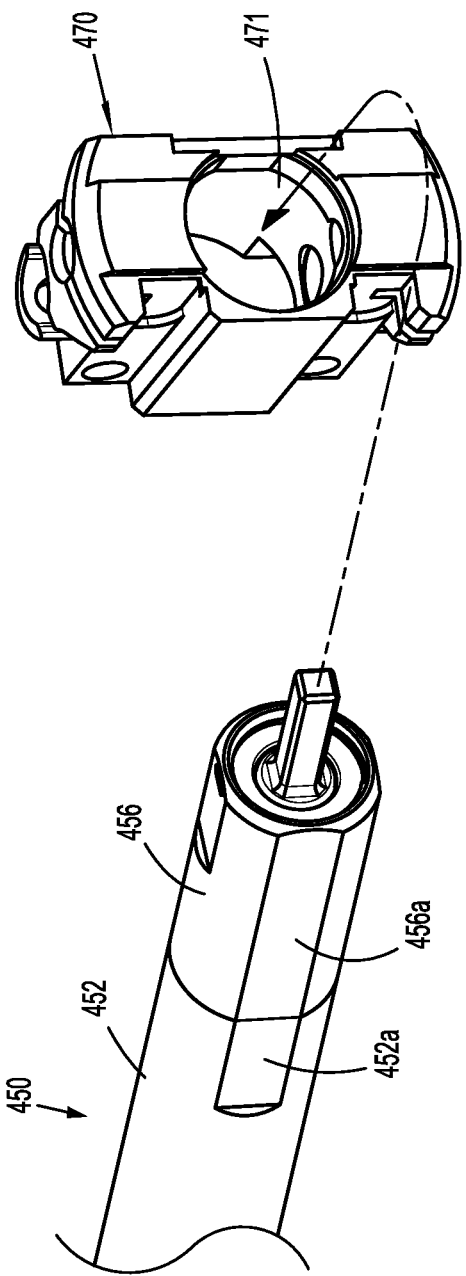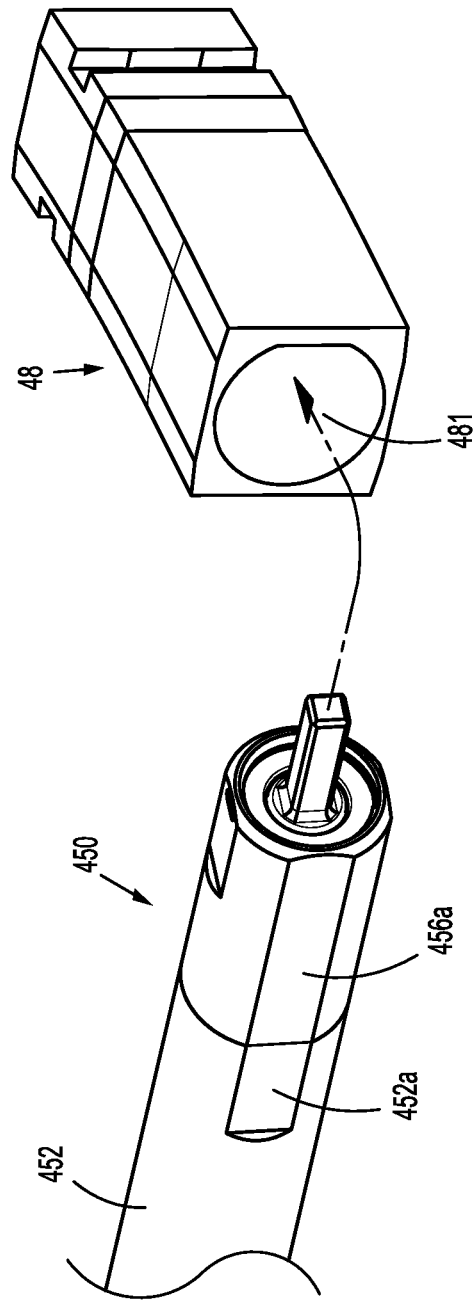

DEVICES AND METHODS FOR ASSEMBLING ADAPTER ASSEMBLIES

CROSS-REFERENCE TO RELATED APPLICATIONS

This application claims the benefit of and priority to U.S. Provisional Patent Application Ser. No. 62/812,554 filed Mar. 1, 2019, the entire disclosure of which is incorporated by reference herein.

BACKGROUND

Technical Field

The present disclosure relates to circular stapling instruments. More particularly, the present disclosure relates to devices and methods for facilitating insertion and alignment of trocar assemblies within adapter assemblies for circular stapling instruments.

Background of Related Art

Surgical instruments for applying staples, clips, or other fasteners to tissue are well known. Typically, endoscopic stapling instruments include an actuation unit, e.g., a handle assembly for actuating the instrument, an elongate shaft for accessing a body cavity, and a tool assembly disposed at a distal end of the elongate shaft.

Adapter assemblies used with a circular stapling tool assembly typically include a trocar assembly for selectively positioning an anvil assembly relative to a cartridge assembly. To facilitate sterilization and reuse of the adapter assemblies, many adapter assemblies include a removable trocar assembly. Subsequent to cleaning and sterilizing, and prior to reuse, the adapter assemblies need to be reassembled by hospital staff or other personnel. Ensuring that the adapter assembly is fully and properly reassembled is important for functionality and patient safety of the circular stapling instruments.

SUMMARY

A device for loading a trocar assembly within an adapter assembly of a surgical stapling instrument is provided. The trocar loading device includes a base member and an engagement member. The base member defines a longitudinal passage for receiving a trocar assembly. The engagement arm is secured to the base member and is configured to releasably secure the trocar assembly within the base member.

In embodiments, the base member includes a connector portion configured to facilitate alignment of the trocar loading device with an adapter assembly. The connector portion may include a first cylindrical section and a second cylindrical section. The first cylindrical section may be configured for receipt within a distal end of an adapter assembly. The second cylindrical section may be configured to act as a stop member for preventing over-insertion of the first cylindrical section into the distal end of the adapter assembly. The base member may include a handle portion configured for operable engagement by a user.

In some embodiments, the engagement arm includes an elongate portion, a C-shaped flange portion disposed on a first end of the elongate portion, and a locking portion extending from the flange portion. The engagement arm may further includes a release tab extending from the flange portion. The engagement arm may be formed from a single piece of material. The engagement arm may be secured to the base member by the screw. The engagement arm includes an inclined surface to facilitate receipt of a trocar assembly within the base member. The base member may include tapered section to accommodate flexing of the engagement arm.

An adapter assembly for connecting a loading unit and an anvil assembly to a powered handle assembly is also provided. The adapter assembly includes an elongate body defining a longitudinal passage and including a strain member disposed along the longitudinal passage, and a trocar assembly configured to be releasably received within the longitudinal passage of the elongate body. The trocar assembly includes a housing and a spring received within a cutout in the housing. The spring is configured to be compressed as the trocar assembly is received within the longitudinal passage to bias the trocar assembly from within the longitudinal passage.

Another adapter assembly for connecting a loading unit and an anvil assembly to a powered handle assembly is provided. The adapter assembly includes an elongate body defining a longitudinal passage, a retainer housing disposed within the elongate body, and a yolk housing disposed within the elongate body the retainer housing. Each of the retainer housing and yolk housing define a longitudinal opening and include a flattened inner surface. The adapter assembly further includes a trocar assembly releasably received within longitudinal passage of the elongate body and through the longitudinal opening of the retainer housing and the yolk housing. The trocar assembly includes a trocar housing and a bearing housing. The trocar housing includes a flattened outer surface corresponding to the flattened inner surface of the retainer housing and is configured for receipt within the longitudinal opening of the retainer housing. The bearing housing includes a flattened outer surface corresponding to the flattened inner surface of the yolk housing and is configured for receipt within the longitudinal opening of the yolk housing.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 3 is a side, perspective view of a trocar loading device according to an embodiment of the present disclosure and the trocar assembly shown in FIG. 2;

FIG. 4 is a side, perspective view of the trocar loading device shown in FIG. 3 with components separated;

FIG. 5 is a side, perspective view of the trocar assembly shown in FIG. 3 secured to the trocar loading device shown in FIG. 3;

FIG. 6 is a top, perspective view of the trocar assembly and the trocar loading device shown in FIG. 5;

FIG. 7 is a cross-sectional side view of the trocar assembly and the trocar loading device as shown in FIG. 3, with a trocar member in an advanced position;

FIG. 8 is a cross-sectional side view taken along line 7-7 shown in FIG. 5;

FIG. 14 is a side, perspective view of the trocar assembly and trocar loading device shown in FIG. 12 secured together;

FIG. 15 is a cross-sectional side view taken along line 15-15 shown in FIG. 14;

FIG. 16 is an enlarged view of trocar assembly and trocar loading unit shown in FIG. 12 secured to a distal end of the adapter assembly shown in FIG. 2 with the trocar loading device engaged with the trocar assembly;

FIG. 17 is an enlarged view of trocar assembly and trocar loading unit shown in FIG. 12 secured to the distal end of the adapter assembly shown in FIG. 16 with the trocar loading device disengaged from the trocar assembly;

FIG. 20 is an end, perspective view of a trocar assembly according to another embodiment of the present disclosure and a retainer housing configured to engage the trocar assembly;

FIG. 21 is an end, perspective view of the trocar assembly shown in FIG. 20 and a yolk housing configured to engage the trocar assembly.

DETAILED DESCRIPTION

Figure 1:
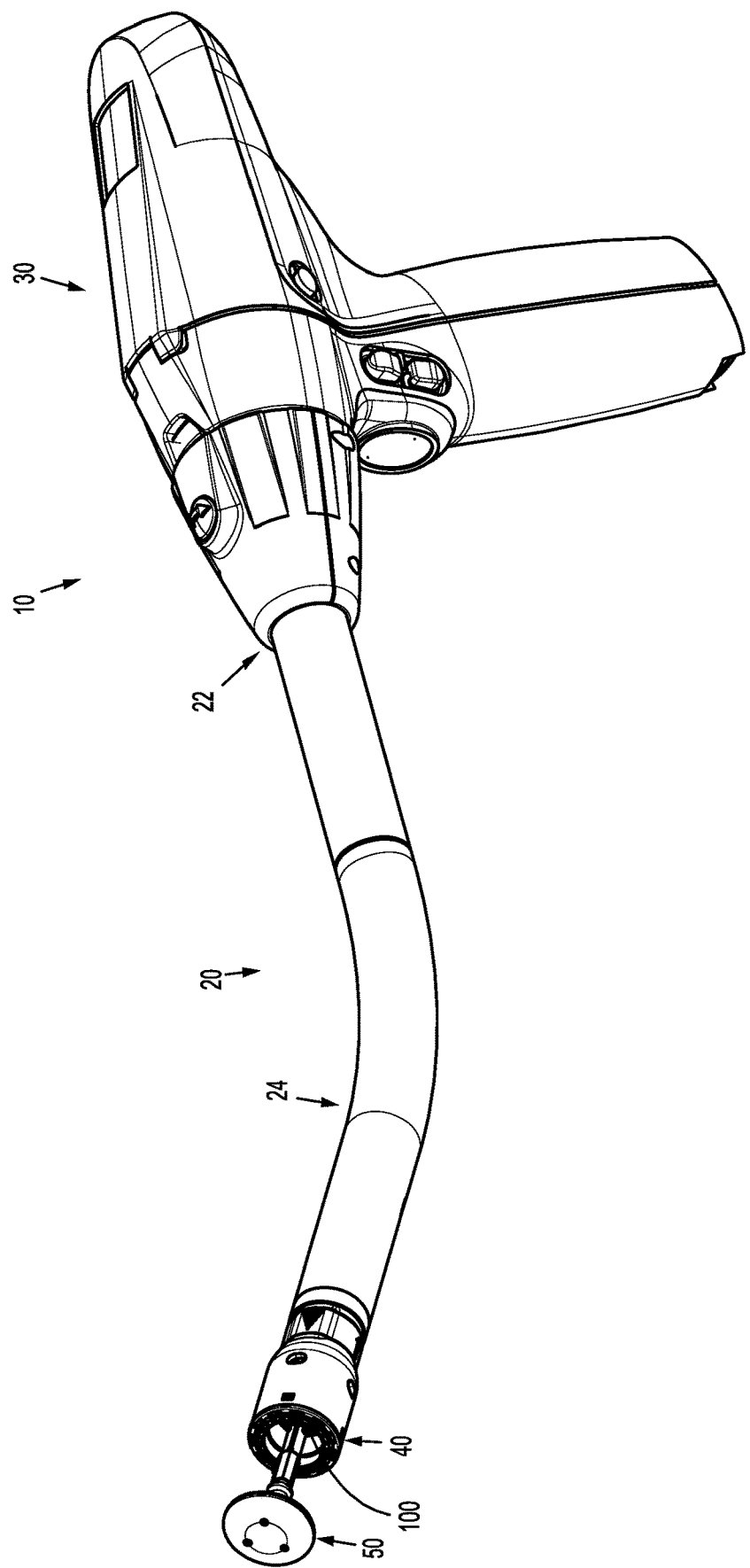
FIG. 1 is a perspective view of a surgical stapling instrument including an adapter assembly and a trocar assembly securable within the adapter assembly by a trocar loading device according to an embodiment of the present disclosure.

Embodiments of the presently disclosed devices and methods for facilitating assembly of a trocar assembly with an adapter assembly will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component farther away from the user.

Referring initially to FIG. 1, an adapter assembly suitable for use with the devices and methods of the present disclosure, shown generally as adapter assembly 20, is a component of a surgical stapling instrument 10. The surgical stapling instrument 10 further includes a powered handle assembly 30, a loading unit 40, and an anvil assembly 50. Although shown and described with reference to the surgical stapling instrument 10 and the adapter assembly 20, the aspects of the present disclosure may be modified for use with surgical stapling instruments having alternative configurations. For a detailed description of exemplary powered surgical stapling instruments, please refer to commonly owned U.S. Pat. No. 9,023,014 ("the '014 patent) and U.S. Pat. No. 9,055,943 ("the '943 patent"), the content of each of which is incorporated by reference herein in its entirety.

The adapter assembly 20 of the surgical stapling instrument 10 will only be described to the extent necessary to fully disclose the aspects of the present disclosure. For a detailed description of exemplary adapter assemblies, please refer to commonly owned U.S. Pat. App. Pub. Nos. 2016/0106406 ("the '406 publication) and 2017/0086879 ("the '879 publication"), the contents of which are incorporated by reference herein in their entirety.

Figure 2:
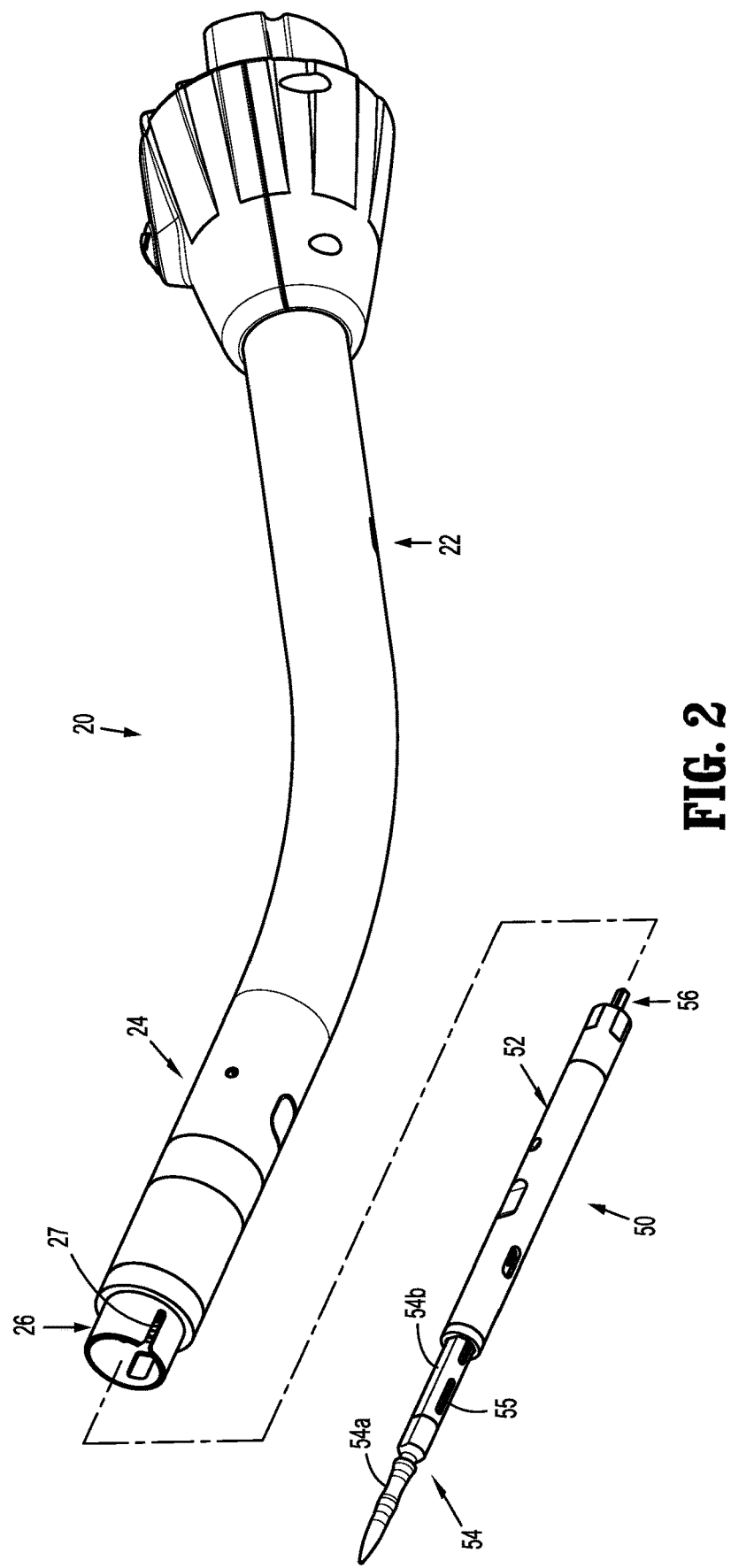
FIG. 2 is a perspective view of the adapter assembly and the trocar assembly of the surgical stapling instrument shown in FIG. 1 with components separated.

With additional reference to FIG. 2, the adapter assembly 20 of the surgical stapling instrument 10 includes a proximal portion 22 configured for operable connection to the handle assembly 30 (FIG. 1) and a distal portion 24 configured for operable connection to the loading unit 40 (FIG. 1). Although shown and described as forming an integral unit, it is envisioned that the proximal and distal portions 22, 24 of the adapter assembly 20 may be formed as separate units that are releasably securable to one another. The distal portion 24 of the adapter assembly 20 includes a connection member 26 for releasably connecting the loading unit 40 with the adapter assembly 20. As described in further detail below, the connector member 26 defines an alignment slot 27 for receiving an alignment feature 116 of the trocar loading device 100.

A removable trocar assembly configured for use with the devices and methods of the present disclosure, shown generally as trocar assembly 50, is releasably securable within the distal portion 24 of the adapter assembly 20. The trocar assembly 50 will only be described to the extent necessary to fully disclose the aspects of the present disclosure. For a detailed description of an exemplary trocar assembly, please refer to the '879 publication.

The removable trocar assembly 50 includes a housing 52, a trocar member 54 slidably disposed within the housing 52, and a drive member 56 (FIG. 8) operably received within the trocar member 54 for axially moving the trocar member 54 relative to the housing 52. A tapered distal portion 54a of the trocar member 54 is configured for releasable connection by the anvil assembly 50 (FIG. 1) of the surgical stapling instrument 10 (FIG. 1). A body portion 54b of the trocar member 54 defines an engagement slot 55. As will be described in further detail below, the engagement slot 55 receives a flange 146 of an engagement arm 104 of a trocar loading device 100.

With reference now to FIGS. 3-8, a device for holding and aligning the trocar assembly 50 with the adapter assembly 20 according an embodiment of the present disclosure is shown generally as trocar loading device 100. The trocar loading device 100 includes a base member 102 and an engagement arm 104 secured to the base member 102 by a screw 106. The base member 102 is configured to receive a proximal portion of the trocar assembly 50 and to align the trocar assembly 50 with the distal portion 24 (FIG. 2) of the adapter assembly 20, as described below. The engagement arm 104 of the trocar loading device 100 is configured to align the trocar assembly 50 with the base member 102 of the trocar loading device 100 and to releasably secure the trocar assembly 50 with the base member 110, as described below.

With continued reference to FIGS. 3-8, the base member 102 of the trocar loading device 100 includes a connector portion 110 configured to facilitate alignment of the trocar loading device 100 with the adapter assembly 20, a receiving portion 120 configured to receive the trocar assembly 50, and a handle portion 130 configured for operable engagement by a user. Although shown as being integrally formed, any or all of the connector portion 110, the receiving portion 120, and the handle portion 130 may be formed as separate components that are secured together using known methods.

The connector portion 110 of the base member 102 of the trocar loading device 100 includes a first cylindrical section 112 and a second cylindrical section 114. The first cylindrical section 112 of the connector portion 110 of the base member 102 is configured to be received within the connector member 26 of the distal portion 24 of the adapter assembly 20. The first cylindrical section 112 includes an alignment feature 116 that is received within the slot 27 in the connector member 26 of the adapter assembly 20 to align the trocar loading device 100 with the adapter assembly 20. The second cylindrical section 114 of the connector portion 110 of the base member 102 acts as a stop member for preventing over-insertion of the of first cylindrical section 114 of the connector portion 110 of the base member 102 into the connector member 26 of the adapter assembly 100 (FIG. 2).

The receiving portion 120 of the base member 102 of the trocar loading device 100 includes an elongate body 122 having a contoured section 124 and a tapered section 126. The contoured section 124 of the elongate body 122 is configured to facilitate engagement by a user of the trocar loading device 100 when separating the trocar loading device 100 from the trocar assembly 50 subsequent to the trocar assembly 50 being secured to the adapter assembly 20 (FIG. 2). As described below, the tapered section 126 of the elongate body 122 accommodates flexing of the engagement arm 104 of the trocar loading device 100 during attachment to and separation of the trocar assembly 50 from the trocar loading device 100.

The elongate body 122 of the base member 102 defines a longitudinal passage 121 configured to receive the trocar member 54 of the trocar assembly 50. An open distal end of the elongate body 122 facilitates cleansing and sterilization of the trocar assembly 50 while secured to the trocar loading device 100. The elongate body 122 of the base member 102 also defines a cutout 123a for accommodating a flange 140 of the engagement arm 104 and a slot 123b for receiving a locking portion 144 of the engagement arm 104. In embodiments, and as shown, the elongate body 122 of the base member 102 defines a threaded opening 125 for receiving the screw 106 for securing the engagement arm 104 to the base member 102.

In embodiments, the elongate body 122 includes flush ports 127 for permitting cleansing and sterilization of the trocar assembly 50 while the trocar loading device 100 is secured to the trocar assembly 50.

Although shown as a substantially planar body 132 that extends radially outward from the receiving portion 120 of the base member 102, the handle portion 130 of the base member 102 may include any configuration to facilitate handling by a user. The planar body 132 of the base member 102 enables the trocar loading device 100, with the trocar assembly 20 secured thereto, to be maintained in an upright, standing position to accommodate placement of the trocar assembly 50 during handling and prior to assembly with the adapter assembly 20, without risk of contaminating and/or compromising the sterility of the trocar assembly 50.

The engagement arm 104 of the trocar loading device 100 includes an elongate portion 140, a C-shaped flange portion 142 disposed on a first end of the elongate portion 140, and a locking portion 144 extending from the flange portion 142. A release tab 146 extends from the flange portion 142. The engagement arm 104 may be integrally formed from a single piece of material. In embodiments, the engagement arm 104 is formed of stamped sheet metal or molded plastic.

In embodiments, and as shown, the engagement arm 104 of the trocar loading device 100 is secured to the base member 102 by the screw 106 received through an opening 141 formed in a second end of the elongate portion 140 of the engagement arm 104. The engagement arm 104 is configured such that when the elongate portion 140 is secured to the base member 102, the flange portion 142 of the engagement arm 104 is received within the cutout 123a of the base member 102 and the locking portion 144 of the engagement arm 104 is received within the slot 123b in the base member 102. The tapered section 126 of the base member 102 permits flexing of the engagement arm 104 to move the locking portion 144 of the engagement arm 104, as indicated by arrow "A" in FIG. 7, out of the slot 123a in the base member 102.

The locking portion 144 of the engagement arm 104 includes an inclined surface 144a to facilitate receipt of the trocar assembly 50 within the receiving portion 120 of the base member 102. More particularly, the inclined surface 144a of the engagement arm 104 of the trocar loading device 100 engages the trocar assembly 50 as the trocar assembly 50 is received with the longitudinal passage 121 of the base member 102 of the trocar loading device 100 to cause inward flexing of the engagement arm 104. In this manner, the locking portion 144 of the engagement arm 104 is moved from within the slot 123a in the base member 102 of the trocar loading device 100 to permit receipt of the trocar assembly 50 within the base member 102 of the trocar loading device 100.

Referring now to FIGS. 7 and 8, the trocar assembly 50 is secured to the trocar loading device 100 by receiving the trocar member 54 in the longitudinal passage 121 of the base member 102 and aligning the slot 55 in the trocar member 54 with the cutout 125 in the base member 102 to permit receipt of the engagement portion 144 of the engagement arm 104 into the slot 55 in the trocar member 54. As the trocar assembly 50 is received within the longitudinal passage 121, the inclined surface 144a of the engagement portion 144 engages the trocar member 54 to cause the engagement arm 102 of the trocar loading device 100 to flex, as indicated by arrow "A" in FIG. 7, to permit receipt of the trocar assembly 50 within the base member 102. Once the slot 55 in the trocar member 54 is aligned with the engagement portion 144 of the engagement arm 104, the engagement arm 104 returns to its unflexed position (FIG. 8) and the engagement portion 144 is received through the slot 127 in the base member 102 and through the slot 55 in the trocar member 54 to secure the trocar assembly 50 within the longitudinal passage 121 of the base member 102.

Figure 9:
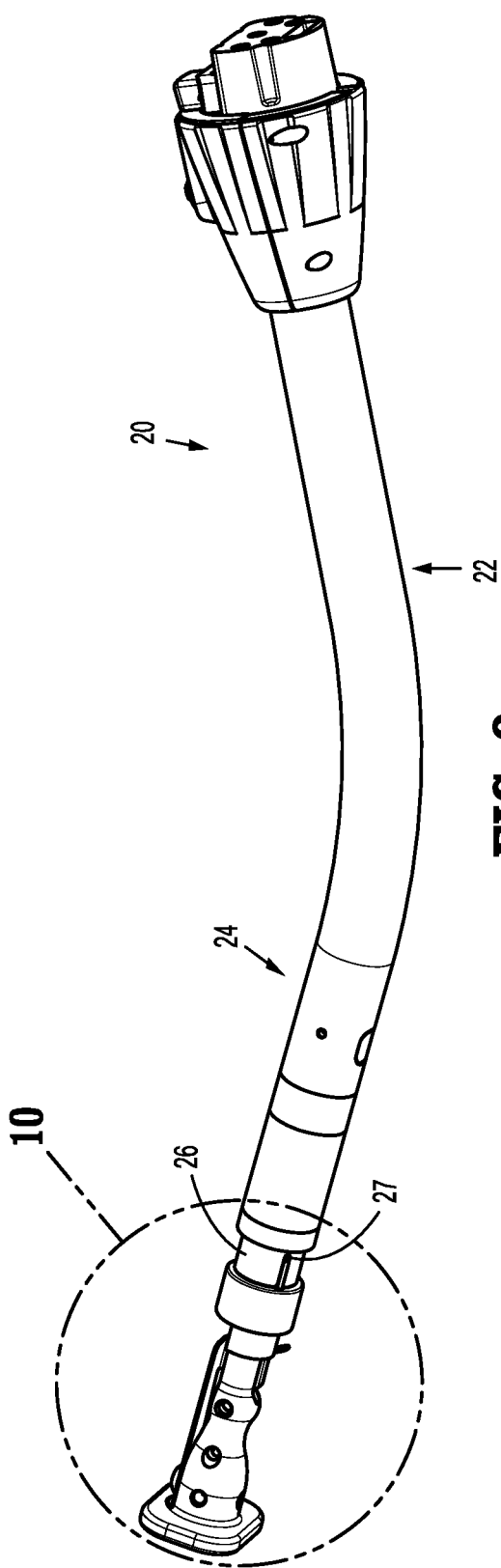
FIG. 9 is a side, perspective view of the trocar assembly and the trocar loading unit shown in FIG. 3 in operable engagement with the adapter assembly shown in FIG. 2.
Figure 10:
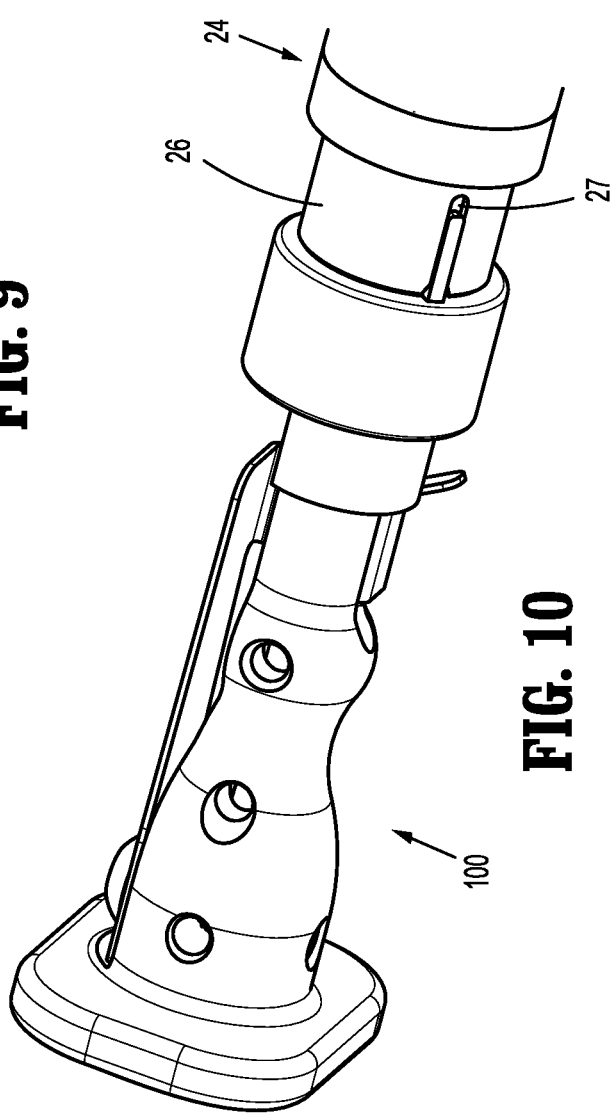
FIG. 10 is an enlarged view of the indicated area of detail shown in FIG. 9.
Figure 11:
FIG. 11 is a side, perspective view of the trocar assembly and the adapter assembly shown in FIG. 9 secured together.
Figure 12:
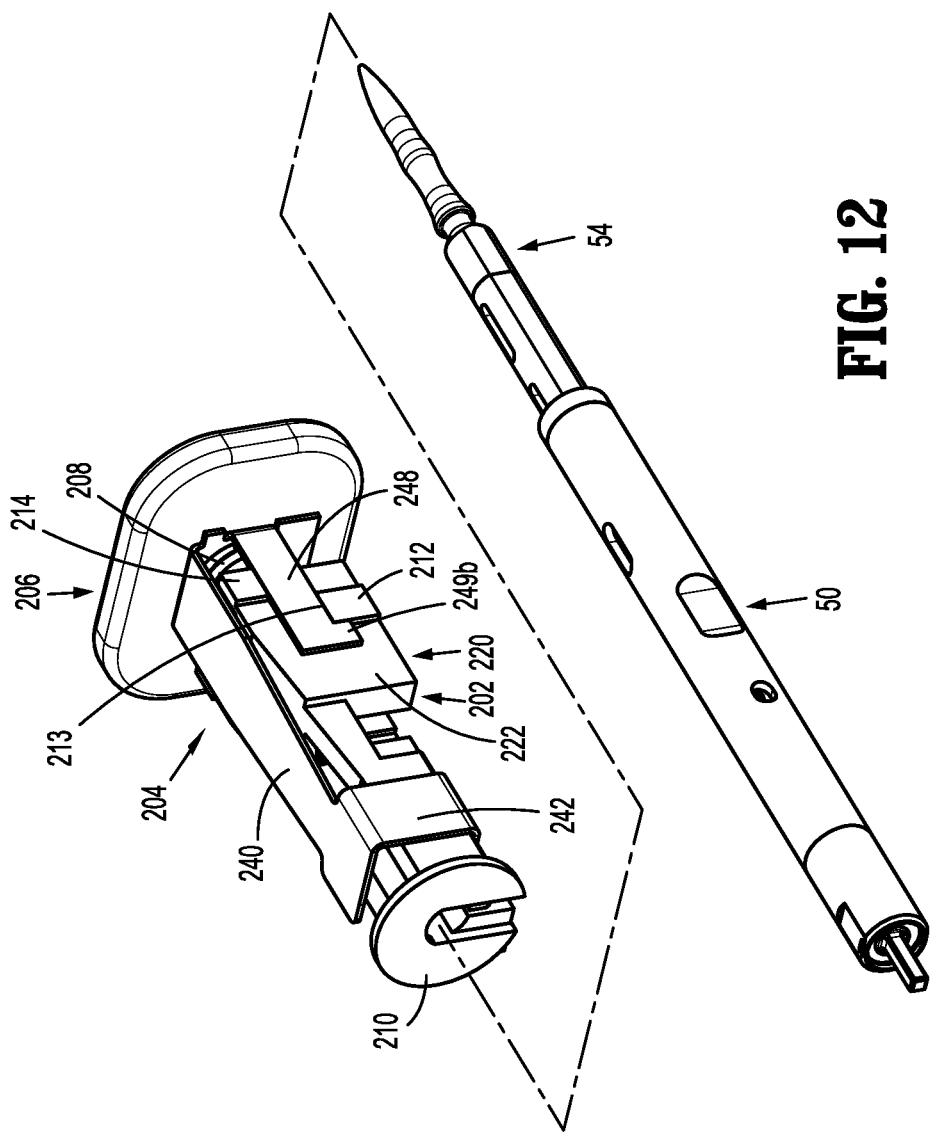
FIG. 12 is a side, perspective view of the trocar assembly shown in FIG. 2 and a trocar loading device according to another embodiment of the present disclosure.
Figure 13:
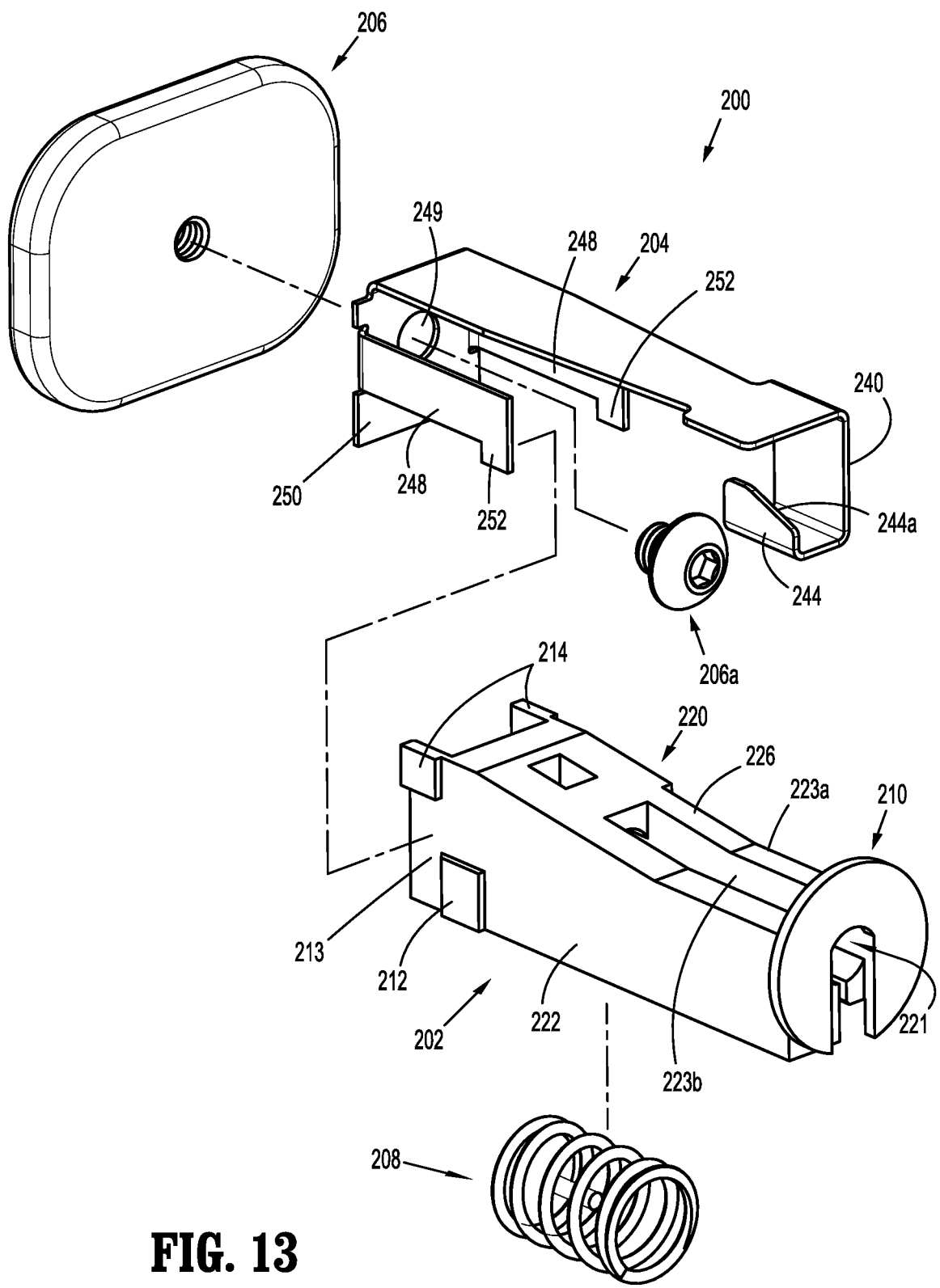
FIG. 13 is a side, perspective view of the trocar loading device shown in FIG. 12 with components separated.

Turning to FIGS. 9 and 10, once the trocar loading device 100 is secured to the trocar assembly 50, the trocar loading device 100 may be used to secure the trocar assembly 50 to the adapter assembly 20. The trocar assembly 20 is secured to the adapter assembly 20 by receiving the first cylindrical section 112 of the connector portion 110 of the base member 102 of the trocar loading device 100 within the connector member 26 of the adapter assembly 20. Proper alignment of the trocar assembly 50 with the adapter assembly 20 is ensured when the alignment feature 116 on the first cylindrical section 112 is received within the alignment slot 27 of the connector member 26. As noted above, the second cylindrical section 114 of the connector portion 110 of the base member 102 acts as a stop to prevent over-insertion of the trocar assembly 50 within the adapter assembly 20. In embodiments, the adapter assembly 20 may provide an audible or tactile indication that the trocar assembly 50 is secured to the adapter assembly 20.

Once the trocar assembly 50 is secured to the adapter assembly 20, the trocar loading device 100 is separated from the adapter assembly 20 and the trocar assembly 50 by first flexing the engagement arm 104 by engaging the tab portion 146 to move the projection portion 144 from within the slot 55 in the trocar member 54 of the trocar assembly 50 and then sliding the trocar loading device 100 longitudinally away from the adapter assembly 20 and from about the trocar assembly 50.

After securing the trocar assembly 50 within the adapter assembly 20, operation of the adapter assembly 20 is substantially similar to operation of the exemplary adapter assemblies shown and described in the '879 publication, previously incorporated by reference herein in its entirety.

With reference now to FIGS. 12-19, another embodiment of a device for holding and aligning the trocar assembly 50 is shown generally as trocar loading device 200. The trocar loading device 200 is substantially similar to trocar loading device 100 described above, and therefore will only be described in detail as it relates to the differences therebetween.

The trocar loading device 200 includes a base member 202, an engagement member 204 received about the base member 202, and a holding member 206 secured to the engagement member 204. As will be described below, a spring member 208 biases the base member 202 away from the holding member 206 to spring load the trocar assembly 50 within the trocar loading device 200.

The base member 202 of the trocar loading device 200 includes a flanged proximal portion 210 configured to facilitate alignment of the trocar loading device 200 with the adapter assembly 20 (FIG. 2) and a receiving portion 220 configured to receive the trocar assembly 50. More particularly, the receiving portion 220 includes an elongate body 222 having a tapered section 226. The tapered section 226 accommodates flexing of the engagement member 204 of the trocar loading device 200 during attachment to and separation from the trocar assembly 50 from the trocar loading device 200. The elongate body 222 of the receiving portion 220 of the base member 202 defines a longitudinal passage 221 configured to receive the trocar member 54 (FIG. 12) of the trocar assembly 50. The elongate body 222 of the base member 202 also defines a cutout 223a for accommodating a flange 242 of the engagement member 204 and a slot 223b for receiving a locking portion 244 of the engagement member 204.

First and second sets of projections 212, 214 extend outwardly from the elongate body 222 of the receiving portion 220 of the base member 202. The first and second sets of projections 212, 214 define a channel 213 therebetween. As will be described below, the channels 213 are configured to receive guide arms 248 of the engagement member 204 in a sliding manner.

In embodiments, the elongate body 222 includes flush ports 227 (FIG. 15) for permitting cleansing and sterilization of the trocar assembly 50 while the trocar loading device 200 is secured to the trocar assembly 50.

The engagement member 204 of the trocar loading device 200 includes an elongate portion 240, a C-shaped flange portion 242 disposed on a first end of the elongate portion 240, and a locking portion 244 extending from the flange portion 242. The engagement member 204 further includes the guide arms 248 for securing the engagement member 204 relative to the base member 202. The guide arms 248 extend from a connector portion 250 of the engagement member 204. The connector portion 250 defines an opening 249 for receiving a screw 206a for connecting the engagement member 204 to the holding member 206.

The engagement member 204 of the trocar loading device 200 is configured such that when the engagement member 204 is secured about the base member 202, the flange portion 242 of the engagement member 204 is received within the cutout 223a of the base member 202 and the locking portion 244 of the engagement member 204 is received within the slot 223b in the base member 202. The tapered section 226 of the base member 202 permits flexing of the engagement member 204 to move the locking portion 244 of the engagement member 204 out of the slot 223a in the base member 202.

The locking portion 244 of the engagement member 204 includes an inclined surface 244a to facilitate receipt of the trocar member 54 (FIG. 12) of the trocar assembly 50 within the receiving portion 220 of the base member 202.

The guide arms 248 of the engagement member 204 each include a tang 252 for engaging the first set of projections 212, respectively, on the elongate body 222 of the receiving portion 220 of the base member 202.

As noted above, the engagement member 204 is secured to the holding member 206 by the screw 206a received through the opening 249 in the connector portion 250 of the engagement member 204. The base member 202 is secured relative to the engagement member 204 by with the guide arms 248. More particularly, the engagement member 204 is received about the base member 202 with the guide arms 248 received within the channels 213 defined between the first and second projections 212, 214, respectively, of the base member 202. The tangs 252 on the guide arms 248 retain the engagement member 204 relative to the base member 202. The spring 208 of the trocar loading device 200 is received between the connector portion 250 of the engagement member 204 and the base member 202 to bias the base member 202 relative to the holding member 206.

The trocar loading device 200 operates in a substantially similar manner to the trocar loading device 100 described above. When the trocar assembly 50 is not properly secured by the engagement member 204 of the trocar loading device 200, the bias created by the spring 208 positioned between the base member 202 and the holding member 206 when receiving the trocar assembly 50 within the longitudinal passage 221 of the base member 202 of the trocar loading device 200 causes the trocar assembly to be ejected from within the longitudinal passage 221 of the base member 202.

Figure 18:
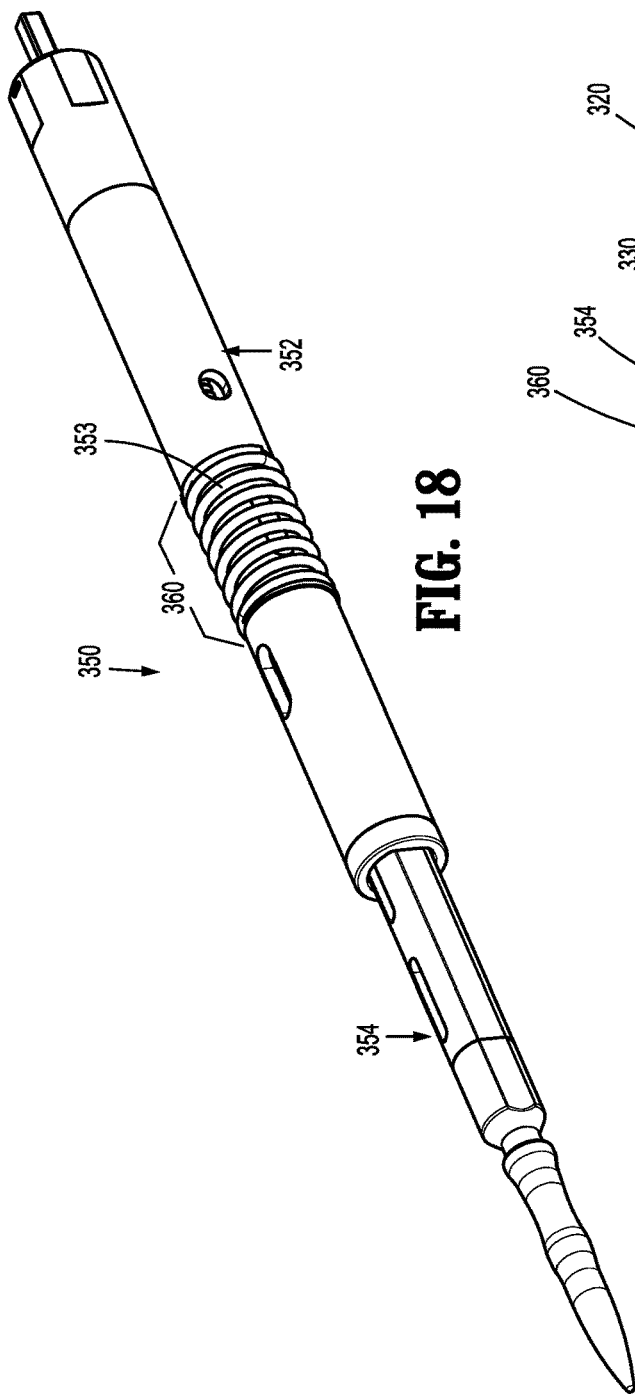
FIG. 18 is a trocar assembly according to an embodiment of the present disclosure.
Figure 19:
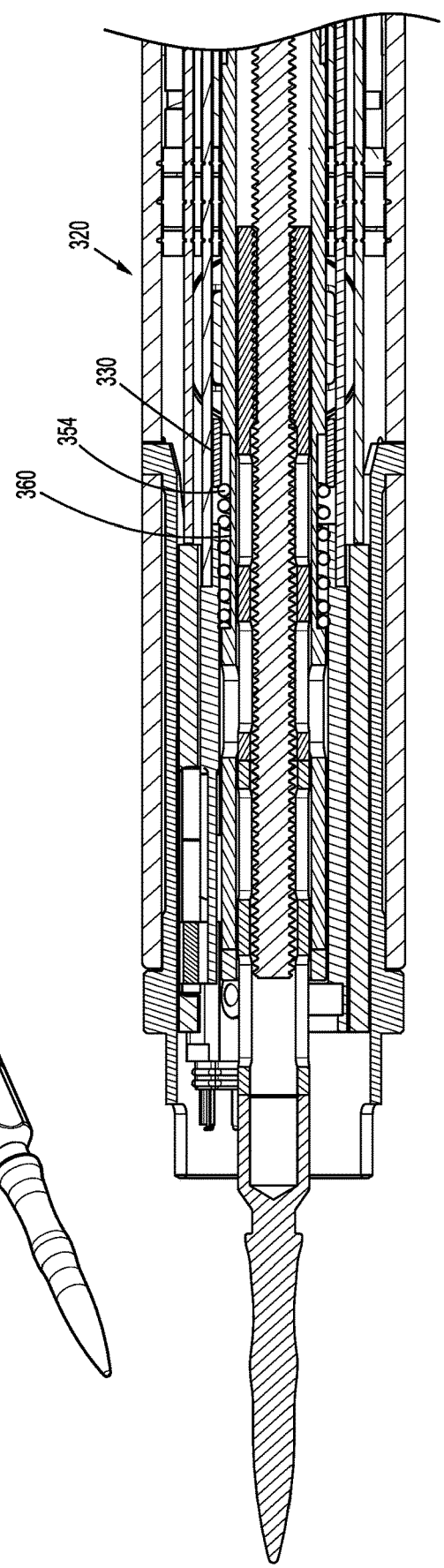
FIG. 19 is a cross-sectional side view of the trocar assembly shown in FIG. 18 secured to an adapter assembly according to an embodiment of the present disclosure.

With reference now to FIGS. 18 and 19, a mechanism for ensuring that a trocar assembly is properly received and secured within an adapter assembly is shown with regards to trocar assembly 350 and adapter assembly 320 (FIG. 19).

Referring initially to FIG. 18, the trocar assembly 350 includes an outer housing 352 and a trocar member 354. The outer housing 352 defines an annular cutout 353 configured for accommodating a compression spring 360. The cutout 353 has a depth and/or the compression spring 360 has a thickness that leaves a portion of the compression spring 360 disposed radially outward of an outer surface 352a of the outer housing 352.

Referring now to FIG. 19, the adapter assembly 320 is configured to releasably receive the trocar assembly 350. A locking mechanism (not shown) secures the trocar assembly 350 within the adapter assembly 320 once the trocar assembly 350 is fully seated within the adapter assembly 320.

A strain mechanism 330 is disposed within the adapter assembly 320 and is configured to engage the compression spring 360 when the trocar assembly 320 is received within the adapter assembly 320. More particularly, during receipt of the trocar assembly 350 within the adapter assembly 320, and prior to the trocar assembly 350 being fully seated within the adapter assembly 320, e.g., engaging a locking mechanism (not shown), the compression spring 360 comes into contact with the strain mechanism 330. Continued insertion of the trocar assembly 350 within the adapter assembly 320 compresses, e.g., loads, the compression spring 360.

In the event that the trocar assembly 350 does not properly seat within the adapter assembly 320 and/or the locking mechanism (not shown) does not properly engage the trocar assembly 350, the loading of the compression spring 360 causes the trocar assembly 350 to be ejected from the adapter assembly 320.

Following a stapling procedure, the trocar assembly 350 may be ejected from the adapter assembly 320 by releasing the trocar assembly 350 from the locking mechanism in a traditional manner.

Figure 22:
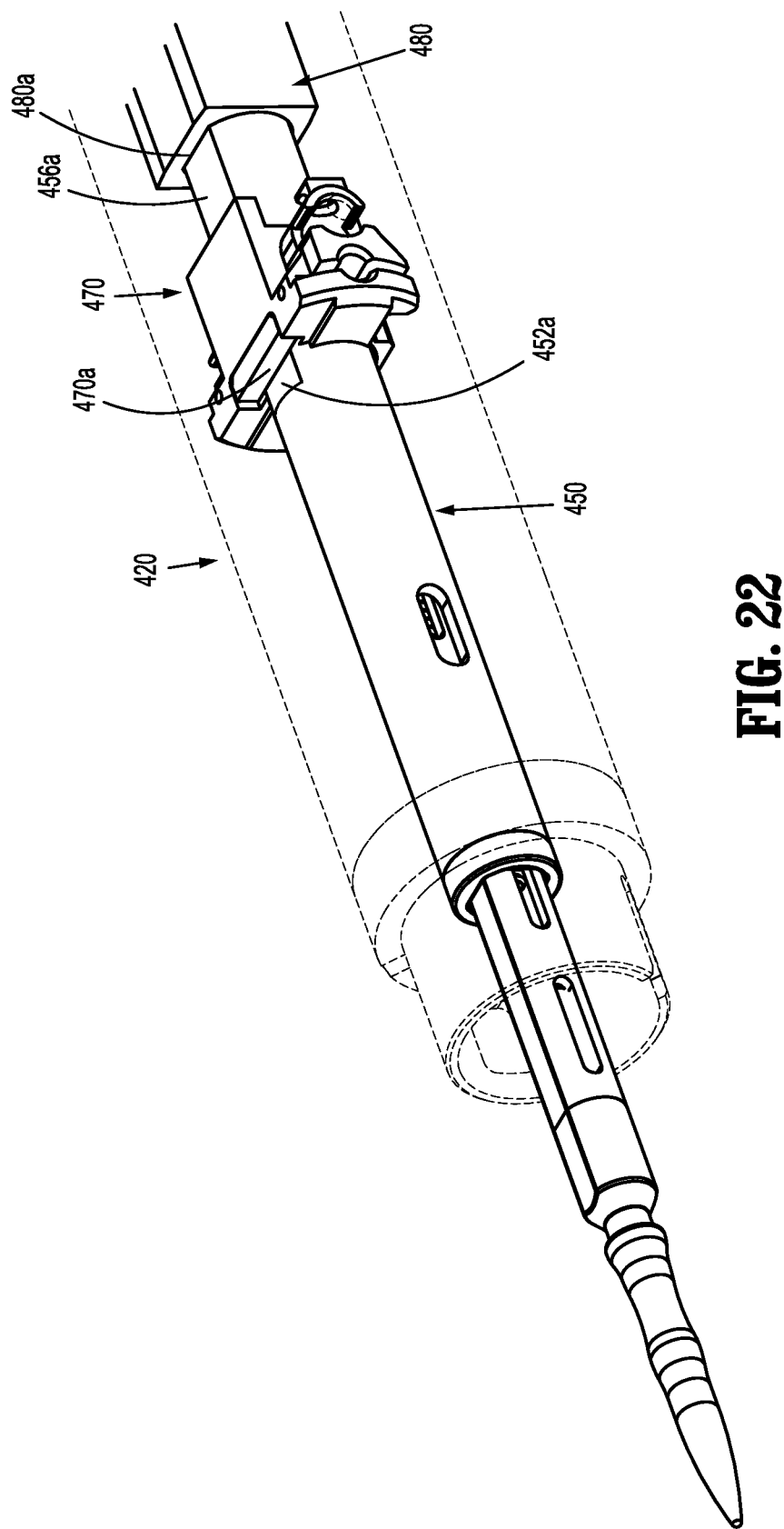
FIG. 22 is an end, perspective view of the trocar assembly shown in FIGS. 20 and 21 secured relative to the retainer housing shown in FIG. 20 and the yolk housing shown in FIG. 21.

With reference now to FIGS. 20-22, mechanisms for assuring alignment of a trocar assembly within an adapter assembly are shown with regards to trocar assembly 450 and adapter assembly 420.

The trocar assembly 450 includes a housing 452 and a bearing housing 456. Each of the housing 452 and the bearing housing 456 includes a flattened portion 452a, 456a, respectively. The flattened portions 452a, 256a of the respective housing 452 and bearing housing 456 are keyed to a flattened portion 470a of a retainer housing 470 (FIG. 20) and a flattened portion 480a of a yolk housing 480 (FIG. 21).

With particular reference to FIG. 20, the retainer housing 470 defines a longitudinal passage 471 for receiving the trocar assembly 450. The flattened portions 452a, 456a of the respective housing 452 and bearing housing 456 and the flattened portion 470a of the retainer housing 470 align with one another to ensure proper orientation of the trocar assembly 450 within the retainer housing 470. Similarly, misalignment of the flattened portions 452a, 456a of the respective housing 452 and bearing housing 456 and the flattened portion 470a of the retainer housing 470 prevent loading of the trocar assembly 450 within the retainer housing 470.

With particular reference to FIG. 21, the yolk housing 480 defines a longitudinal passage 481 for receiving the trocar assembly 450. The flattened portion 456a of the bearing housing 456 and the flattened portion 480a of the retainer housing 480 align with one another to ensure proper orientation of the trocar assembly 450 within the yolk housing 480. Similarly, misalignment of the flattened portion 456a of the bearing housing 456 and the flattened portion 480a of the yolk housing 480 prevent loading of the trocar assembly 450 within the yolk housing 480.

In embodiments, the flattened portions 452a, 456a, 470a, 480a of the respective housing 452, bearing housing 456, retainer housing 470, yolk housing 480 may be formed of metal. The metal construction of the interfacing flattened portions 452a, 456a, 470a, 480a provides a greater feedback to the person assembling the adapter assembly 420, e.g., surgeon, and/or increases the difficulty of forcing the trocar assembly 450 within the adapter assembly 420 when the flattened portions 452a, 456a and flattened portions 470a, 480a are not aligned.

The embodiments of the present disclosure may be used individually or in combination with the embodiments to facilitate proper loading and reloading of a trocar assembly within an adapter assembly.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A trocar loading device comprising:
   a base member defining a longitudinal passage for receiving a distal portion of a trocar member of a trocar assembly and a distal portion of a trocar housing of the trocar assembly, and
   an engagement arm secured to the base member and configured to releasably secure a trocar assembly within the base member.

2. The trocar loading device of claim 1, wherein the base member includes a connector portion configured to facilitate alignment of the trocar loading device with an adapter assembly.

3. The trocar loading device of claim 2, wherein the connector portion includes a first cylindrical section and a second cylindrical section.

4. The trocar loading device of claim 3, wherein the first cylindrical section is configured for receipt within a distal end of an adapter assembly.

5. The trocar loading device of claim 4, wherein the second cylindrical section is configured to act as a stop member for preventing over-insertion of the first cylindrical section into the distal end of the adapter assembly.

6. The trocar loading device of claim 1, wherein the base member includes a handle portion configured for operable engagement by a user.

7. The trocar loading device of claim 1, wherein the engagement arm includes an elongate portion, a C-shaped flange portion disposed on a first end of the elongate portion, and a locking portion extending from the flange portion.

8. The trocar loading device of claim 7, wherein the engagement arm further includes a release tab extending from the flange portion.

9. The trocar loading device of claim 8, wherein the engagement arm is formed from a single piece of material.

10. The trocar loading device of claim 7, wherein the engagement arm includes an inclined surface to facilitate receipt of a trocar assembly within the base member.

11. The trocar loading device of claim 1, wherein the engagement arm is secured to the base member by the screw.

12. The trocar loading device of claim 1, wherein the base member includes a tapered section to accommodate flexing of the engagement arm.

13. A trocar loading assembly comprising:
   a trocar assembly configured to releasably secure an anvil assembly to an adapter assembly, the trocar assembly including a trocar housing having a distal portion, and a trocar member selectively extendable from the trocar housing and having a distal portion, and
   a trocar loading device including:
      a base member defining a longitudinal passage for receiving the distal portion of the trocar member of the trocar assembly and the distal portion of the trocar housing of the trocar assembly; and an engagement arm secured to the base member and configured to releasably secure the trocar assembly within the base member.

14. The trocar loading assembly of claim 13, wherein the base member of the trocar loading device includes a handle portion configured for operable engagement by a user.

15. The trocar loading assembly of claim 13, wherein the engagement arm of the trocar loading device includes an elongate portion, a C-shaped flange portion disposed on a first end of the elongate portion, and a locking portion extending from the flange portion.

16. The trocar loading assembly of claim 15, wherein the engagement arm of the trocar loading device further includes a release tab extending from the flange portion.

17. The trocar loading assembly of claim 16, wherein the engagement arm of the trocar loading device is formed from a single piece of material.

18. The trocar loading assembly of claim 13, wherein the engagement arm of the trocar loading device is secured to the base member by the screw.

19. The trocar loading assembly of claim 13, wherein the base member of the trocar loading device includes tapered section to accommodate flexing of the engagement arm.

20. The trocar loading assembly of claim 19, wherein the engagement arm of the trocar loading device includes an inclined surface to facilitate receipt of the trocar assembly within the base member.

* * * * *